United States Patent
Alruhaimi

(10) Patent No.: US 12,232,756 B2
(45) Date of Patent: Feb. 25, 2025

(54) DUAL BONE FORCEPS

(71) Applicant: KING SAUD UNIVERSITY, Riyadh (SA)

(72) Inventor: Khalid Abdullah Ibrahim Alruhaimi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/662,205

(22) Filed: May 13, 2024

(65) Prior Publication Data

US 2024/0299057 A1 Sep. 12, 2024

Related U.S. Application Data

(63) Continuation of application No. 18/119,967, filed on Mar. 10, 2023.

(51) Int. Cl.
*A61B 17/28* (2006.01)
*A61B 17/285* (2006.01)
*A61B 17/80* (2006.01)

(52) U.S. Cl.
CPC .......... *A61B 17/285* (2013.01); *A61B 17/282* (2013.01); *A61B 17/2833* (2013.01); *A61B 17/808* (2013.01); *A61B 2017/2808* (2013.01)

(58) Field of Classification Search
CPC ... A61B 17/28; A61B 17/2816; A61B 17/282; A61B 17/2833; A61B 17/2841;
(Continued)

(56) References Cited

U.S. PATENT DOCUMENTS 8,425,520 B2 4/2013 Zalenski et al.
8,628,070 B2 1/2014 Neubauer
(Continued)

FOREIGN PATENT DOCUMENTS

CN 103552007 A 2/2014
CN 103932759 A 7/2014

OTHER PUBLICATIONS

Indiamart Bone and Plate Holding Forcep; printed on May 20, 2020 from https://www.indiamart.com/proddetail/bone-and-plate-holding-forcep-7593958791.html.

*Primary Examiner* — Katherine M Rodjom
(74) *Attorney, Agent, or Firm* — Nath, Goldberg & Meyer; Joshua B. Goldberg

(57) ABSTRACT

The dual bone forceps may be considered tandem locking forceps wherein the forceps are coupled to each other so that the surgeon may use one for clamping the bone graft plate adjacent the graft site while clamping the other forceps to a supporting bone structure above, below, or lateral to the graft site during the procedure. The dual bone forceps includes a bone graft plate clamping forceps having clamping jaws at the anterior end and flat handles terminating in locking jaws at the posterior end. The dual bone forceps also includes an anchoring forceps having an elongate hook blade and a shortened anvil blade at the anterior end and locking handles at the posterior end. A linking bar extends non-coplanar from the shortened anvil blade to the pivot of the bone graft plate clamping forceps to maintain the two forceps linked to each other, but spaced apart in different planes.

6 Claims, 4 Drawing Sheets

(58) Field of Classification Search
CPC .............. A61B 17/285; A61B 17/2804; A61B 2017/2837; A61B 2017/2808; A61B 17/808
See application file for complete search history.

(56) References Cited

U.S. PATENT DOCUMENTS

2004/0106927 A1\* 6/2004 Ruffner .............. A61B 17/1671
606/85
2009/0030467 A1 1/2009 Sonohata et al.
2015/0100080 A1 4/2015 Kohler \* cited by examiner

DUAL BONE FORCEPS

CROSS-REFERENCE TO RELATED APPLICATION

This application is a continuation of U.S. patent application Ser. No. 18/119,967, filed on Mar. 10, 2023, the entire contents of which are incorporated herein by reference.

BACKGROUND

1. Field

The disclosure of the present patent application relates to surgical instruments, and particularly to dual bone forceps for use during bone graft procedures.

2. Description of the Related Art

During bone graft operations, conventional surgical forceps are typically used to hold a graft bone block or plate to be inspected, fixed, or approximated to the recipient bone site. A nurse or assistant to the surgeon typically holds this graft bone block or plate for a relatively long time in the required position throughout the entirety of the procedure, including bone drilling, fixation, and filling of the space with bone particles. The help from an assistant may result in movement of the held graft from its original position and changing the sites of screws holes while the surgeon drills and fixes the bone graft with screws and fills the grafted space with bone particles. Since the graft bone block or plate must be held steadily throughout the procedure, the strain on the nurse or surgical assistant can be considerable, and potential unintended movements by the nurse or assistant can result in errors by the surgeon during the procedure. It would be desirable to be able to remove the necessity of having an additional person to hold the graft bone plate during the operation. Thus, a dual bone forceps solving the aforementioned problems is desired.

SUMMARY

The dual bone forceps is a surgical tool for use during bone graft operations and the like. The dual bone forceps may be considered tandem locking forceps wherein a blade of one forceps is coupled to the pivot screw of the other so that the surgeon may use one for clamping the bone graft plate adjacent the graft site while clamping the other forceps to a supporting bone structure above, below, or lateral to the graft site during the procedure. The dual bone forceps includes a bone graft plate clamping forceps having clamping jaws at the anterior end and flat handles terminating in locking jaws at the posterior end. The dual bone forceps also includes an anchoring forceps having an elongate hook blade and a shortened anvil blade at the anterior end and locking handles at the posterior end. A linking bar extends non-coplanar from the shortened anvil blade to the pivot screw of the bone graft plate clamping forceps to maintain the two forceps linked to each other, but spaced apart in different planes.

In use, the surgeon clamps the bone plate or bone block in the jaws of the bone graft plate clamping forceps. The surgeon grips the handles and lifts the anchoring forceps, thereby also raising the bone plate or bone block. The surgeon pivots the arms of the anchoring forceps while maneuvering the clamped bone plate or bone block adjacent to the bone graft site to position the plate or block at a location and in the orientation and spacing desired for fixing the graft with screws and simultaneously hooking the elongate blade to engage an anchoring bone structure above, below, or lateral to the graft site, and then clamping the anchoring forceps to the anchoring bone structure by locking the handles of the anchoring forceps. With the dual bone forceps clamped to the patient's body and the bone plate or bone block rigidly clamped adjacent the graft site, the surgeon has both hands free to complete the procedure and does not require an assistant to hold the graft immobile for extended periods of time, thereby improving the accuracy and precision of drilling and placement of fixation screws or fasteners during the bone graft procedure, and permitting the introduction of bone particles to fill space when needed. The dual bone forceps may be used for orthopedic and maxillofacial surgeries, among others.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The dual bone forceps is a surgical tool for use during bone graft operations and the like. The dual bone forceps may be considered tandem locking forceps wherein a blade of one forceps is coupled to the pivot screw of the other so that the surgeon may use one for clamping the bone graft plate adjacent the graft site while clamping the other forceps to a supporting bone structure above, below, or lateral to the graft site during the procedure. The dual bone forceps includes a bone graft plate clamping forceps having clamping jaws at the anterior end and flat handles terminating in locking jaws at the posterior end. The dual bone forceps also includes an anchoring forceps having an elongate hook blade and a shortened anvil blade at the anterior end and locking handles at the posterior end. A linking bar extends non-coplanar from the shortened anvil blade to the pivot screw of the bone graft plate clamping forceps to maintain the two forceps linked to each other, but spaced apart in different planes.

Figure 1:
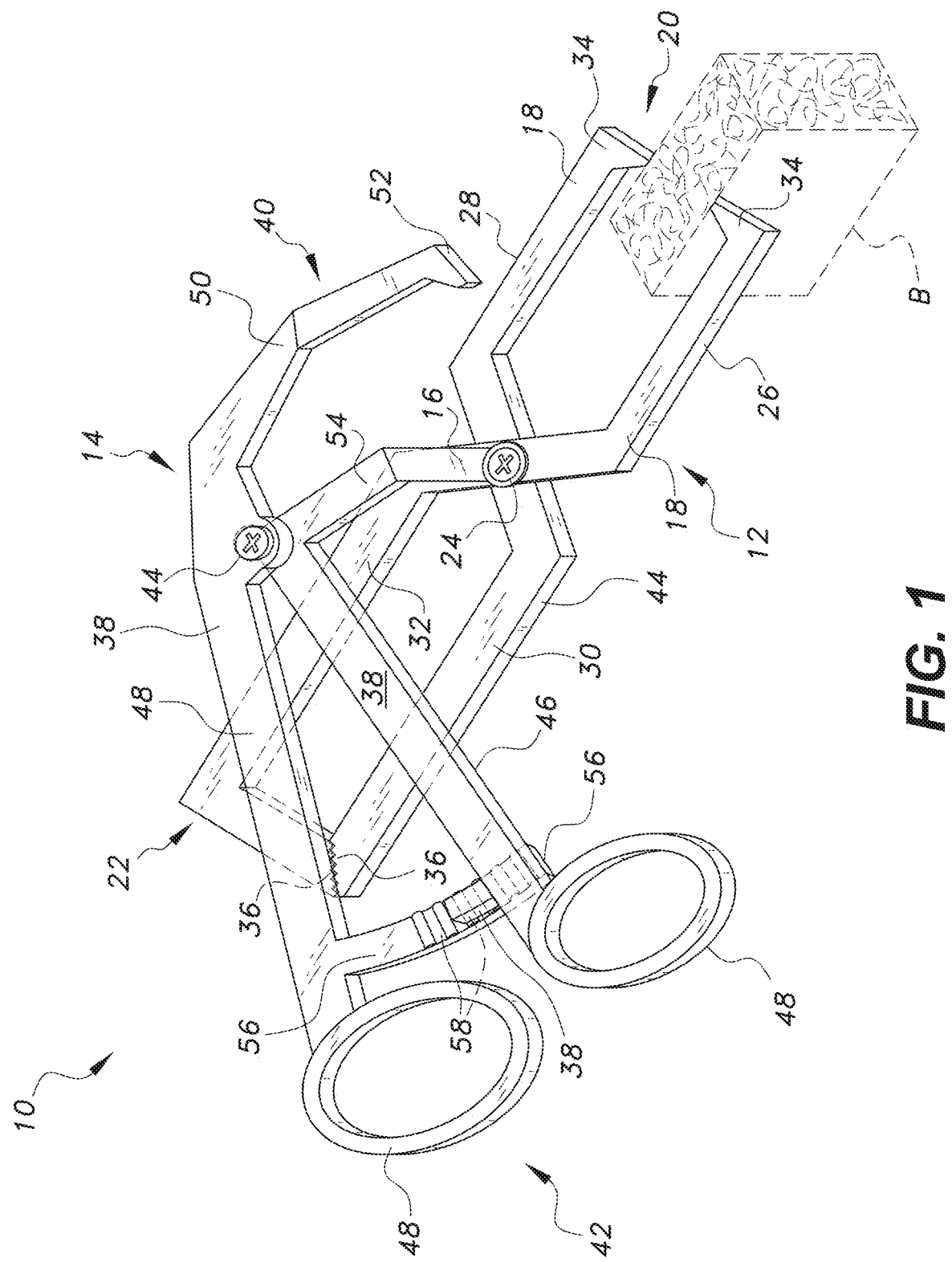
FIG. 1 is an environmental perspective view of dual bone forceps.
Figure 2:
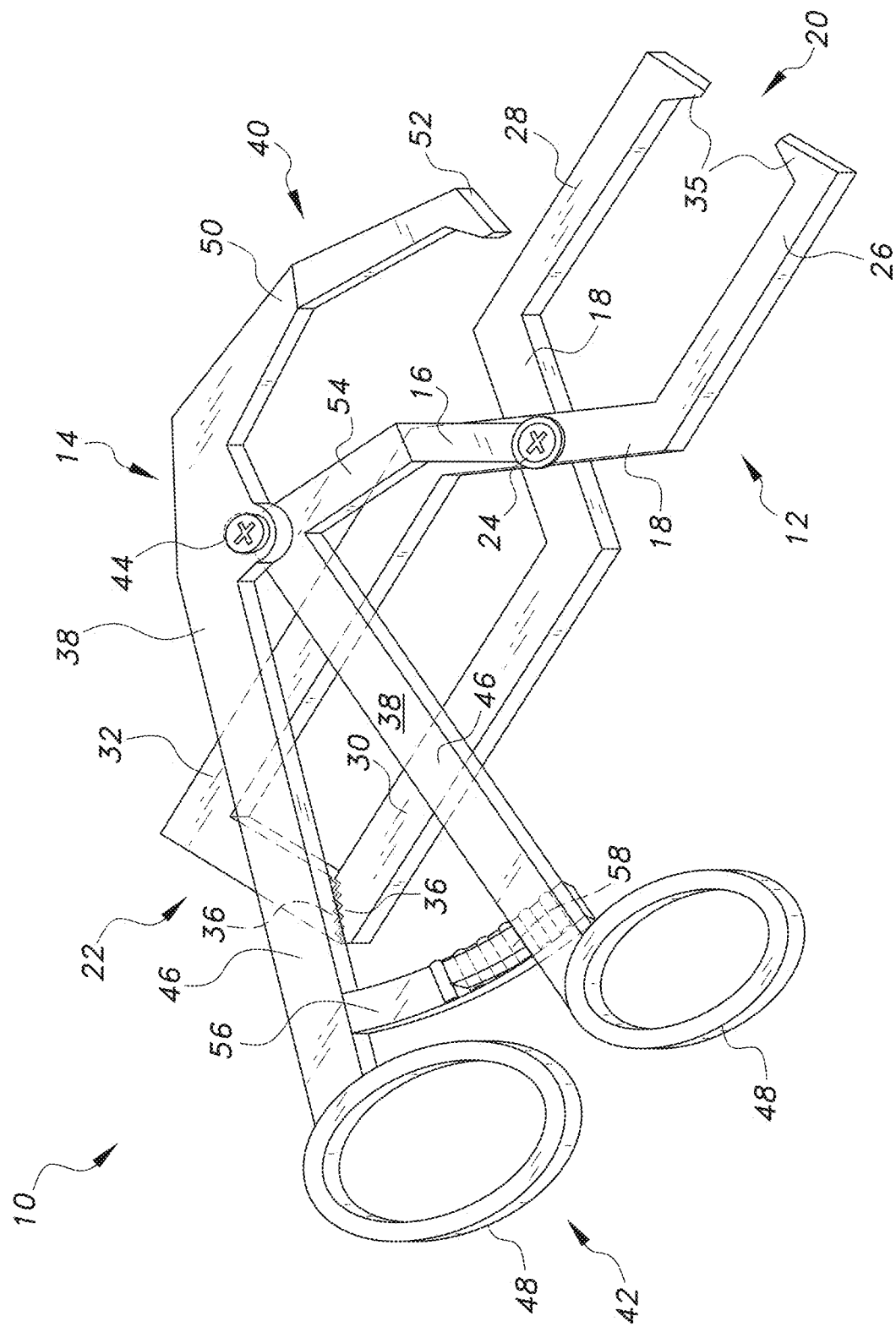
FIG. 2 is a perspective view of the dual bone forceps.

As shown in FIGS. 1 and 2, the dual bone forceps 10 includes a bone graft plate clamping forceps 12 and an anchoring forceps 14 joined to the bone graft plate clamping forceps 12 by a linking bar 16. The bone graft plate clamping forceps 12 is a forceps having a pair of linear arms 18, each of the arms 18 having an anterior end 20 and a posterior end 22. The arms 18 are pivotally joined to each other by a pivot screw, rivet, pivot pin, or other pivoting member 24 between the anterior ends 20 and the posterior ends 22. The arms 18 define clamping blades 26, 28 between the pivot member 24 and the anterior ends 20 and a handle portion or handles 30, 32 between the pivot member 24 and the posterior ends 22. The clamping blades terminate in clamping jaws 34 and the handles 30, 32 terminate in locking jaws 36 having teeth that selectively engage to lock the handles 30, 32 to clamp an object between the clamping jaws 34 and prevent further pivoting of the arms 18 until the locking jaws 36 are released. The clamping jaws 34 are adapted for gripping a bone plate or bone block B between the jaws 34.

The anchoring forceps 14 is a forceps having a pair of arms 38, each of the arms 38 having an anterior end 40 and a posterior end 42. The arms 38 are pivotally joined to each other by a pivot screw, rivet, pivot pin, or other pivoting member 44 between the anterior ends 40 and the posterior ends 42. The arms 38 each define a handle portion or handles 46 between the pivot member 44 and the posterior ends 42, the handles 46 each terminating in finger loops 48 for ease in grasping the handles 46. One of the arms 38 defines an elongated blade between the pivot member 44 and the anterior end 40, forming a hook 50 terminating in a tip 52 slanting backward in the direction of the finger loops 48. The other arm 38 defines a shortened or truncated anvil blade 54 between the pivot member 44 and the anterior end 40. The handles 46 have overlapping arcuate locking plates 56 adjacent the finger loops 48, each of the locking plates 56 having a serrated inner face or selectively interlocking teeth 58 for selectively locking the arms 38 with the hooked blade 50 and the anvil blade 54 clamped onto a supporting bone structure.

The arms 18 of the bone graft plate clamping forceps 12 and the arms 38 of the anchoring forceps 14 pivot in different planes. The bone graft plate clamping forceps 12 and the anchoring forceps 14 are joined and spaced apart by a linking bar 16 that extends non-coplanar from the end of the shortened anvil blade 54 to the pivot member 24 of the bone graft plate clamping forceps 12 to maintain the two forceps linked to each other, but spaced apart in different planes. The linking bar 16 may extend orthogonal to the shortened anvil blade 54 so that the bone graft plate clamping forceps 12 and the anchoring forceps 14 pivot in parallel planes, or the linking bar 16 may extend at an obtuse angle to the shortened anvil blade 54 so that the bone graft plate clamping forceps 12 and the anchoring forceps 14 pivot in planes forming a dihedral angle with respect to one another.

Figure 3:
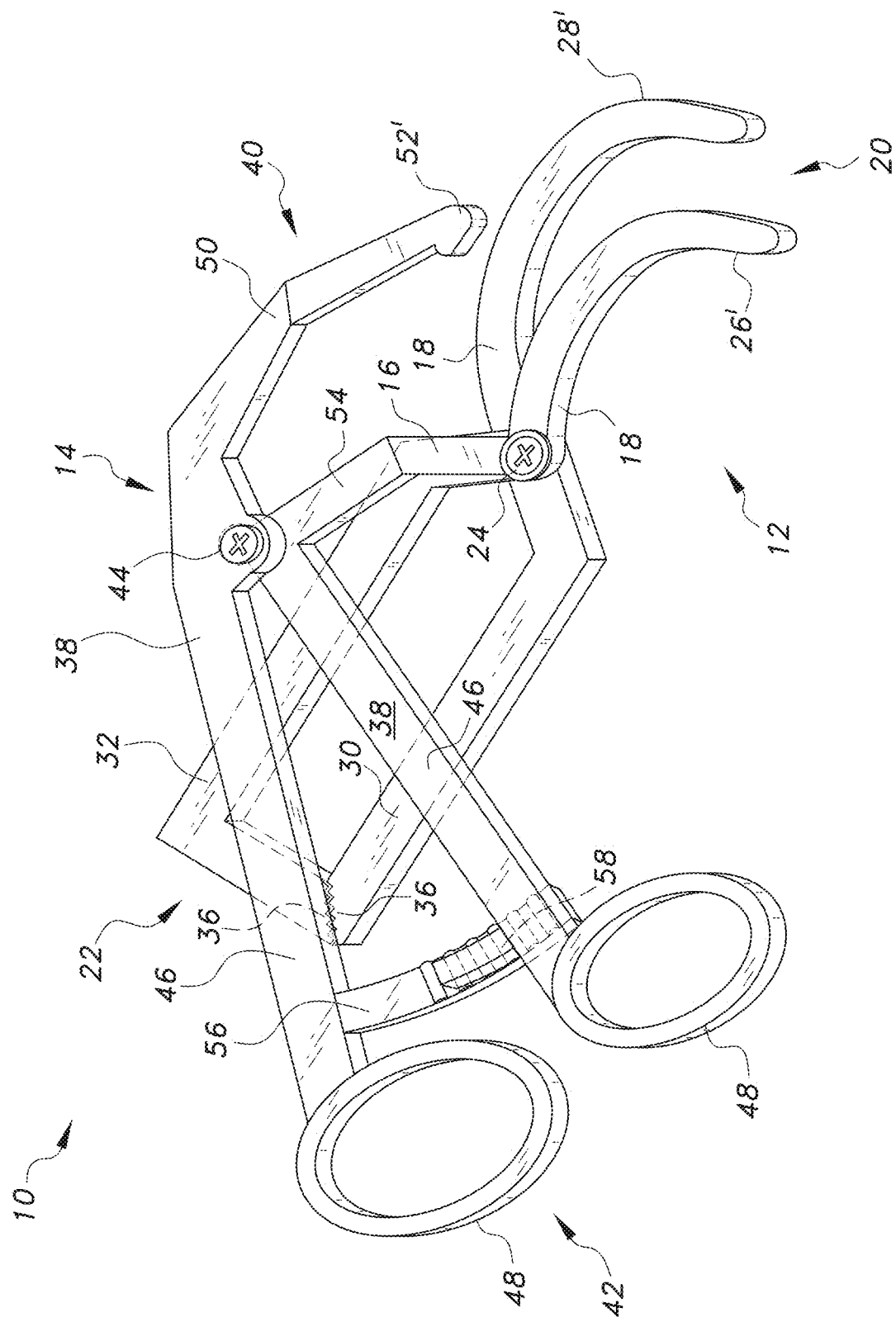
FIG. 3 is a perspective view of an alternative embodiment of the dual bone forceps.

It should be understood that the overall contouring and relative dimensions of arms 18 are shown for exemplary purposes only. As a non-limiting example, FIG. 3 shows an alternative embodiment with rounded arcuate arms 18'. In this embodiment, as a further non-limiting example, tip 52 of hook 50 has also been blunted. It should be understood that the overall contouring and relative dimensions of both bone graft plate clamping forceps 12 and anchoring forceps 14 may be varied dependent upon the particular surgical requirements therefor.

Figure 4:
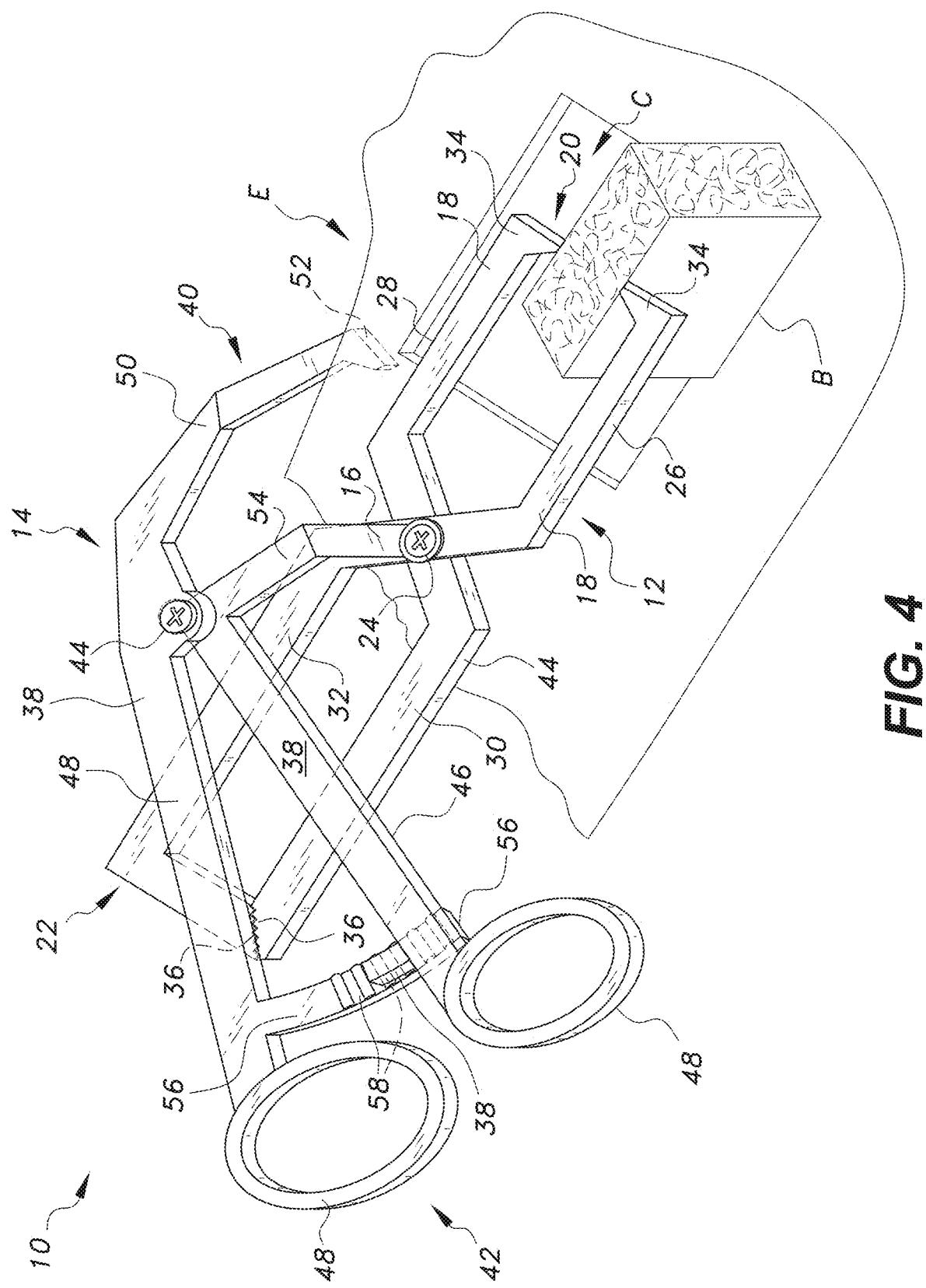
FIG. 4 is an environmental perspective view of the dual bone forceps of FIG. 1.

In use, as shown in FIG. 4, the surgeon clamps the bone plate or bone block B in the jaws 34 of the bone graft plate clamping forceps 12. The surgeon grips the handles and lifts the anchoring forceps 14, thereby also raising the bone plate or bone block B. The surgeon pivots the arms of the anchoring forceps 14 while maneuvering the clamped bone plate or bone block B adjacent to the bone graft site (shown in FIG. 4 as cavity C formed in the bone) to position the plate or block B at a location and in the orientation and spacing desired for fixing the graft with screws and simultaneously hooking the elongate blade to engage an anchoring bone structure above, below, or lateral to the graft site (shown in FIG. 4 as edge E), and then clamping the anchoring forceps 14 to the anchoring bone structure by locking the handles 46 of the anchoring forceps 14. With the dual bone forceps 10 clamped to the patient's body and the bone plate or bone block B rigidly clamped adjacent the graft site (i.e., cavity C), the surgeon has both hands free to complete the procedure and does not require an assistant to hold the graft immobile for extended periods of time, thereby improving the accuracy and precision of drilling and placement of fixation screws or fasteners during the bone graft procedure, and permitting the introduction of bone particles to fill space when needed. The dual bone forceps may be used for orthopedic and maxillofacial surgeries, among others.

It is to be understood that the dual bone forceps is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A dual bone forceps, comprising:
a bone graft plate clamping forceps having:
a pair of arms, each of the arms having an anterior end and a posterior end; and
a pivot member pivotally attaching the arms to each other between the anterior ends and the posterior ends, the arms defining clamping blades extending between the pivot member and the anterior ends, the clamping blades terminating in clamping jaws at the anterior ends, the clamping jaws being adapted for clamping bone graft material therebetween, the arms defining handles extending between the pivot member and the posterior ends of the arms, the handles terminating in locking jaws selectively locking the handles to clamp the bone graft material between the clamping jaws and prevent further pivoting of the arms until the locking jaws are disengaged;
an anchoring forceps having:
a first arm and a second arm, each of the arms having an anterior end and a posterior end; and
a pivot member pivotally attaching the first and second arms of the anchoring forceps to each other between the anterior ends and the posterior ends, each of the arms defining handle portions extending between the pivot member and the posterior ends of the arms, the handle portions terminating in finger loops, each of the handle portions having a locking member extending therefrom, the locking members overlapping and having a serrated inner face to selectively lock the first and second arms in a clamping position, the first arm defining an elongated arcuate, hooked blade between the pivot member and the anterior end, the hooked end terminating in an angled tip, the second arm defining a shortened anvil blade having a length shorter than the hooked blade and terminating in a link end, the anchoring forceps being adapted for clamping to a supporting bone structure adjacent a bone graft site; and
a linking bar extending between the link end of the anvil blade of the anchoring forceps and the pivot member of the bone graft plate clamping forceps, the linking bar spacing the anchoring forceps apart from the bone graft plate clamping forceps so that the anchoring forceps holds the bone graft plate clamping forceps with the bone graft material adjacent the bone graft site to leave a surgeon with both hands free to fix the bone graft material to the bone graft site, wherein the linking bar extends orthogonal to the anvil blade, whereby the anchoring forceps and the bone graft plate clamping forceps pivot in parallel planes.

2. The dual bone forceps as recited in claim 1, wherein the arms of said bone graft plate clamping forceps are flat and linear.

3. The dual bone forceps as recited in claim 1, wherein the angled tip at the hooked end of the first arm of said anchoring forceps points back toward the finger loops.

4. The dual bone forceps according to claim 1, wherein the bone graft material comprises a bone graft plate.

5. The dual bone forceps according to claim 1, wherein the bone graft material comprises a bone block.

6. A dual bone forceps, comprising:
- a first locking forceps having clamping blades, the first locking forceps being adapted for clamping a bone graft material;
- a second locking forceps, the second locking forceps being adapted for clamping to a supporting bone structure adjacent a bone graft site; and
- a linking member connecting the first locking forceps and the second locking forceps in tandem so that the second locking forceps is adapted for clamping to a patient while holding the first locking forceps supporting the bone graft material adjacent a bone graft site during a bone graft procedure, wherein:

said first locking forceps has a pivot member pivotally attaching the clamping blades to each other; and said second locking forceps has an elongated first blade and a truncated second blade shorter than the elongated first blade, the linking member extending between the truncated second blade of said second locking forceps and the pivot member of said first locking forceps, whereby the first locking forceps and the second locking forceps pivot in parallel planes.

* * * * *